US010421928B2

(12) United States Patent
Eiting et al.

(10) Patent No.: US 10,421,928 B2
(45) Date of Patent: Sep. 24, 2019

(54) CLEANING AGENT CONTAINING PROTEASES

(71) Applicant: Henkel AG & Co. KGaA, Duesseldorf (DE)

(72) Inventors: Thomas Eiting, Duesseldorf (DE); Nina Mussmann, Willich (DE); Thorsten Bastigkeit, Wuppertal (DE); Noelle Wrubbel, Duesseldorf (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 14/927,609

(22) Filed: Oct. 30, 2015

(65) Prior Publication Data

US 2016/0097021 A1 Apr. 7, 2016

Related U.S. Application Data

(63) Continuation of application No. PCT/EP2014/058176, filed on Apr. 23, 2014.

(30) Foreign Application Priority Data

Apr. 30, 2013 (DE) ........................ 10 2013 207 933

(51) Int. Cl.
*C11D 3/386* (2006.01)
*C12N 9/54* (2006.01)

(52) U.S. Cl.
CPC .......... *C11D 3/386* (2013.01); *C11D 3/38681* (2013.01); *C12N 9/54* (2013.01); *C12Y 304/21062* (2013.01)

(58) Field of Classification Search
None
See application file for complete search history.

(56) References Cited

U.S. PATENT DOCUMENTS 5,474,699 A * 12/1995 Ahmed .................... C11D 3/06 510/226
5,527,483 A * 6/1996 Kenkare .................. C11D 3/08 435/219
6,432,902 B1 * 8/2002 Aquino .............. C11D 3/38672 435/174
2004/0248273 A1 * 12/2004 Noerregaard-Madsen .................. C12N 9/54 435/222
2012/0172280 A1 * 7/2012 Knotzel ................. C11D 3/386 510/392
2012/0238005 A1 * 9/2012 Wieland ................. C11D 3/361 435/264

FOREIGN PATENT DOCUMENTS

EP 2216393 A1 8/2010
EP 2551335 A1 1/2013
WO 2009/021867 A2 2/2009
WO 2011/072117 A1 6/2011

OTHER PUBLICATIONS

PCT International Search Report (PCT/EP2014/058176) dated Oct. 14, 2014.
Bender et al., "The Determination of the Concentration of Hydrolytic Enzyme Solutions: a-Chymotrypsin, Trypsin, Papain, Elastase, Subtilisin, and Acetylcholinesterase", Journal of the American Chemical Society, vol. 88:24, pp. 5890-5913, 1966.
Altschul et al., "Basic Local Alignment Search Tool", Journal of Molecular Biology, vol. 215, pp. 403-410, 1990.
Altschul et al., "Gapped BLAST and PSI-BLAST: A New Generation of Protein Database Search Programs", Nucleic Acids Research, vol. 25, No. 17, pp. 3389-3402, 1997.

* cited by examiner

*Primary Examiner* — Paul J Holland
(74) *Attorney, Agent, or Firm* — Thomas G. Krivulka

(57) ABSTRACT

The present invention relates to a cleaning agent having improved cleaning performance wherein the agent comprises a first protease and a second protease and to a cleaning method, particularly an automatic cleaning method in which this agent is used.

4 Claims, No Drawings

Specification includes a Sequence Listing.

CLEANING AGENT CONTAINING PROTEASES

FIELD OF THE INVENTION

The present invention generally relates to a cleaning agent, preferably a dishwashing agent, especially an automatic dishwashing agent, which comprises at least two proteases, and to the use of such a cleaning agent.

BACKGROUND OF THE INVENTION

The most important criterion when cleaning textiles, hard surfaces, such as in particular when washing dishes, in particular during automatic dish washing, is the cleaning performance when it comes to a wide variety of soiling, which is introduced in particular in the form of food residue. While the cleaning performance of dishwashing agents used today is generally high, the problem that arises, among other things due to the general trend in automatic dishwashing to increasingly use low-temperature programs, is that many of the usual automatic dishwashing agents exhibit inadequate cleaning performance on tenacious, burnt soiling. Such inadequate cleaning performance and the therewith resulting inadequate cleaning of the dishes result in dissatisfaction on the part of the consumer and in the consumer pretreating tenacious soiling, which in turn increases the consumption of water and energy. As a result, a general need exists for automatic dishwashing agents that exhibit good cleaning performance even on tenacious, in particular burn-on, soiling, without reducing the existing good cleaning performance when it comes to other types of soiling.

It was therefore the object of the present invention to provide a cleaning agent, preferably a dishwashing agent, especially an automatic dishwashing agent, which exhibits enhanced cleaning performance of such soiling, without the cleaning performance being reduced when it comes to other types of soiling.

Surprisingly, it has now been established that the use of a combination of different proteases considerably improves the cleaning performance of corresponding cleaning agents, preferably of a dishwashing agent, especially an automatic dishwashing agent on protease-sensitive stains, in particular burnt food soiling, in particular burnt sugar-containing food soiling.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A cleaning agent, characterized by comprising at least one first protease and one second protease, wherein a) the first protease comprises an amino acid sequence that is at least 80% identical to the amino acid sequence indicated in SEQ ID NO. 1 over the entire length thereof and includes at least one amino acid substitution at one of the positions 9, 15, 66, 212 and 239 using the numbering according to SEQ ID NO. 1; and b) the second protease is selected from the group consisting of b1) protease comprising an amino acid sequence that is at least 80% identical to the amino acid sequence indicated in SEQ ID NO. 2 over the entire length thereof and includes the amino acid glutamic acid (E) at position 99 using the numbering according to SEQ ID NO. 2; b2) protease comprising an amino acid sequence that is at least 80% identical to the amino acid sequence indicated in SEQ ID NO. 2 over the entire length thereof and includes the amino acid substitution R99E using the numbering according to SEQ ID NO. 2 in combination with at least two further amino acid substitutions, which are selected from the group consisting of S3T, V4I, and V199I; and b3) protease comprising an amino acid sequence that is at least 80% identical to the amino acid sequence indicated in SEQ ID NO. 1 over the entire length thereof and includes the amino acid substitution S99A using the numbering according to BPN' in combination with an insertion between positions 99 and 100, wherein the inserted amino acid is aspartic acid (D).

Use of a combination of a first protease and a second protease for improving the cleaning performance, in particular the cleaning performance on enzyme-sensitive stains, of a cleaning agent, preferably of an automatic dishwashing agent, characterized in that a) the first protease comprises an amino acid sequence that is at least 80% identical to the amino acid sequence indicated in SEQ ID NO. 1 over the entire length thereof and includes at least one amino acid substitution at one of the positions 9, 15, 66, 212 and 239 using the numbering according to SEQ ID NO. 1; and b) the second protease is selected from the group consisting of b1) protease comprising an amino acid sequence that is at least 80% identical to the amino acid sequence indicated in SEQ ID NO. 2 over the entire length thereof and comprises the amino acid glutamic acid (E) at position 99 using the numbering according to SEQ ID NO. 2; b2) protease comprising an amino acid sequence that is at least 80% identical to the amino acid sequence indicated in SEQ ID NO. 2 over the entire length thereof and includes the amino acid substitution R99E using the numbering according to SEQ ID NO. 2 in combination with at least two further amino acid substitutions, which are selected from the group consisting of S3T, V4I, and V199I; and b3) protease comprising an amino acid sequence that is at least 80% identical to the amino acid sequence indicated in SEQ ID NO. 1 over the entire length thereof and includes the amino acid substitution S99A using the numbering according to BPN' in combination with an insertion between positions 99 and 100, wherein the inserted amino acid is aspartic acid (D).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

In a first aspect, the present invention is directed to a cleaning agent for hard surfaces, in particular a dishwashing agent, especially an automatic dishwashing agent, which comprises a first protease and a second protease, wherein a) the first protease comprises an amino acid sequence that is at least 80% identical to the amino acid sequence indicated in SEQ ID NO. 1 over the entire length thereof and includes at least one amino acid substitution at one of the positions 9, 15, 66, 212 and 239 using the numbering according to SEQ ID NO. 1, and b) the second protease is selected from the group consisting of b1) protease comprising an amino acid sequence that is at least 80% identical to the amino acid sequence indicated in SEQ ID NO. 2 over the entire length thereof and comprises the amino acid glutamic acid (E) at position 99 using the numbering according to SEQ ID NO. 2; b2) protease comprising an amino acid sequence that is at least 80% identical to the amino acid sequence indicated in SEQ ID NO. 2 over the entire length thereof and includes the amino acid substitution R99E using the numbering according to SEQ ID NO. 2 in combination with at least two further amino acid substitutions, which are selected from the group consisting of S3T, V4I, and V199I; and b3) protease comprising an amino acid sequence that is at least 80% identical to the amino acid sequence indicated in SEQ ID NO. 1 over the entire length thereof and includes the amino acid substitution S99A using the numbering according to BPN' in combination with an insertion between positions 99 and 100, wherein the inserted amino acid is aspartic acid (D).

When using the agent, such a combination of multiple proteases results in significantly enhanced cleaning performance when it comes to tenacious stains.

A further object of the present invention is the use of a cleaning described herein, preferably a dishwashing agent, especially an automatic dishwashing agent in a cleaning method, preferably a dishwashing method, especially in an automatic dishwashing method, preferably the use for improving the cleaning performance, in particular the cleaning performance on protease-sensitive stains, on hard surfaces, in particular dishes when cleaning the same, preferably in an automatic dishwasher, in particular burnt, tenacious soiling, among other things also at temperatures that are lower than the customarily used temperatures.

A further object of the present invention is a cleaning method, preferably a dishwashing method, especially an automatic dishwashing method, in which a cleaning agent described herein, preferably a dishwashing agent, especially an automatic dishwashing agent, is used in particular for the purpose of improving the cleaning performance when it comes to burnt, protease-sensitive stains. In various embodiments of the invention, temperatures that are lower than the customarily used temperatures are used in the dishwashing method.

"Low temperatures" or "temperatures that are lower than the customarily used temperatures," as used herein in the context of dishwashing methods, preferably refers to temperatures below 60° C., in particular below 55° C., still more preferably 50° C. or lower, particularly preferably 45° C. or lower, and most preferably 40° C. or lower. This temperature information refers to the temperatures used in the washing steps.

These and further aspects, features and advantages of the invention become apparent to a person skilled in the art when studying the following detailed description and claims. Every feature from one aspect of the invention may be used in another aspect of the invention. Moreover, it goes without saying that the examples contained herein are intended to describe and illustrate the invention, but do not limit the same, and in particular the invention is not limited to these examples. All percentage information is percent by weight, unless indicated otherwise. Numerical ranges indicated in the format "from x to y" include the mentioned values. If several preferred numerical ranges are indicated in this format, it goes without saying that all ranges resulting from the combination of the different end points are likewise covered.

The proteases used are alkaline serine proteases. They act as non-specific endopeptidases, which is to say they hydrolyze arbitrary acid amide bonds that lie in the interior of peptides or proteins, thereby causing the decomposition of protein-containing soiling on the goods to be cleaned. The pH optimum of these is usually in the distinctly alkaline range.

The sequences of the mature protease subtilisin 309 from Bacillus lentus, which is sold under the trade name Savinase® by Novozymes A/S, Bagsvaerd, Denmark, or of the mature alkaline protease from Bacillus lentus DSM 5483 (wild type) are indicated in SEQ ID NO. 1 and SEQ ID NO. 2, respectively.

"Different," as used herein with reference to the proteases, refers to proteases that differ in terms of the amino acid sequence thereof. In various embodiments, proteases that are different from each other originate from different types of organisms or differ from each other by mutations, for example those created artificially.

"Variant," as used herein in the context of proteases, refers to natural or artificially created variations of a native protease which have an amino acid sequence that is modified compared to the reference form. Such a variant may have single or multiple point mutations, which is to say substitutions of one amino acid naturally occurring at the corresponding position by another, insertions (introduction of one or more amino acids) and/or deletions (removal of one or more amino acids), in particular one or more point mutations. Such variants preferably have at least 50%, preferably 60% or more, still more preferably 70%, 80%, 90%, 100% or more of the enzyme activity of the reference form. In various embodiments, such a variant has an amino acid sequence that is at least 70%, preferably 75%, 80%, 85%, 90%, 95%, 96%, 97%, 98% or 99% identical to the sequence serving as the reference across the entire length thereof. The variants preferably have the same length as the reference sequence. Variants may stand out compared to the reference form by improved properties, such as higher enzyme activity, higher stability, changed substrate specificity, and the like. Only variants exhibiting protease activity are used.

The identity of nucleic acid or amino acid sequences is determined by a sequence comparison. This sequence comparison is based on the BLAST algorithm that is established in the prior art and customarily used (see, for example, Altschul, S. F., Gish, W., Miller, W., Myers, E. W. & Lipman, D. J. (1990) "Basic local alignment search tool." J. Mol. Biol. 215:403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, pgs. 3389-3402) and is essentially carried out by associating similar successions of nucleotides or amino acids in the nucleic acid or amino acid sequences with each other. A tabular association of the particular positions is referred to as alignment. Another algorithm available in the prior art is the FASTA algorithm.

Such a comparison also allows information to be provided about the similarity of the compared sequences among each other. It is customarily indicated in percent identity, which is to say the share of identical nucleotides or amino acid residues at the same positions or at positions corresponding to each other in an alignment. The broader concept of homology, in the case of amino acid sequences, takes conserved amino acid exchanges into consideration, which is to say amino acids having similar chemical activity, since these generally carry out similar chemical activities within the protein. The similarity of the compared sequences may thus also be indicated in percent homology or percent similarity. Identity and/or homology information can be provided for entire polypeptides or genes, or only for individual regions. Homologous or identical regions of different nucleic acid or amino acid sequences are therefore defined by agreement in the sequences. Such regions often have identical functions. They may be small and comprise only few nucleotides or amino acids. Such small regions often carry out functions that are essential for the overall activity of the protein. It may therefore be useful to relate sequence agreement only to individual, optionally small regions. Unless indicated otherwise, however, identity or homology information in the present application refers to the entire length of the respective indicated nucleic acid or amino acid sequence.

The first protease used within the meaning of the present invention is a protease comprising an amino acid sequence that is at least 80% identical to the amino acid sequence indicated in SEQ ID NO. 1 over the entire length thereof and includes at least one amino acid substitution at one of the positions 9, 15, 66, 212 and 239 using the numbering according to SEQ ID NO. 1.

The first protease used may thus be a variant of subtilisin 309 from Bacillus lentus including the amino acid sequence indicated in SEQ ID NO. 1, which is at least 80% identical to the amino acid sequence indicated in SEQ ID NO. 1 over the entire length thereof and includes at least one amino acid substitution at one of the positions 9, 15, 66, 212 and 239 using the numbering according to SEQ ID NO. 1. Preferably proteases are used which have an amino acid substitution at two, preferably three, in particular four, most particularly preferably five of the above-mentioned positions.

Particularly preferably a variant including at least one, preferably two, in particular three, particularly preferably four, or most particularly preferably 5 of the amino acid substitutions selected from S9R, A15T, V66A, N212D and Q239R, based on the numbering according to SEQ ID NO. 1, is used. Such a variant has the amino acid sequence indicated in SEQ ID NO. 3.

Other variants that may be used are those which include an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence indicated in SEQ ID NO. 3, wherein positions 9, 15, 66, 212 and 239 are invariable, which is to say the amino acid corresponds to the corresponding amino acid in SEQ ID NO. 3 at these positions.

The second protease is different from the first protease, which is to say a protease that is covered both by the definition of the first protease and that of the second protease cannot simultaneously be considered a first protease and a second protease.

The second protease b) is selected from the group

- b1) protease comprising an amino acid sequence that is at least 80% identical to the amino acid sequence indicated in SEQ ID NO. 2 over the entire length thereof and comprises the amino acid glutamic acid (E) at position 99 using the numbering according to SEQ ID NO. 2;
- b2) protease comprising an amino acid sequence that is at least 80% identical to the amino acid sequence indicated in SEQ ID NO. 2 over the entire length thereof and includes the amino acid substitution R99E using the numbering according to SEQ ID NO. 2 in combination with at least two further amino acid substitutions, which are selected from the group consisting of S3T, V4I, and V199I; and
- b3) protease comprising an amino acid sequence that is at least 80% identical to the amino acid sequence indicated in SEQ ID NO. 1 over the entire length thereof and includes the amino acid substitution S99A using the numbering according to BPN' in combination with an insertion between positions 99 and 100, wherein the inserted amino acid is aspartic acid (D).

A second essential component of cleaning agents according to the invention is the protease b), selected from proteases b1), b2) and b3).

The protease b1) preferably comprises an amino acid sequence that is at least 80%, and increasingly preferably at least 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 99% identical to the amino acid sequence indicated in SEQ ID NO. 2 over the entire length thereof and comprises the amino acid glutamic acid (E) at position 99 using the numbering according to SEQ ID NO. 2. A most particularly preferred protease in this regard is indicated in SEQ ID NO. 4.

The protease b2) preferably comprises an amino acid sequence that is at least 80%, and increasingly preferably at least 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 98.8% identical to the amino acid sequence indicated in SEQ ID NO. 2 over the entire length thereof and includes the amino acid substitution R99E using the numbering according to SEQ ID NO. 2 in combination with at least two further amino acid substitutions, which are selected from the group consisting of S3T, V4I and V199I. A most particularly preferred protease in this regard is indicated in SEQ ID NO. 5.

The protease b3) preferably comprises an amino acid sequence that is at least 80%, and increasingly preferably at least 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 99% identical to the amino acid sequence indicated in SEQ ID NO. 1 over the entire length thereof and includes the amino acid substitution S99A using the numbering according to BPN' in combination with an insertion between positions 99 and 100, wherein the inserted amino acid is aspartic acid (D). A particularly preferred protease in this regard is indicated in SEQ ID NO. 6.

Further preferred proteases are proteases as described above, which moreover comprise the amino acid leucine (L) at position 211 using the numbering according to SEQ ID NO. 2.

Particularly preferred cleaning agents according to the invention are characterized in that the protease b1) comprises an amino acid sequence that is at least 99% identical to the amino acid sequence indicated in SEQ ID NO. 2 over the entire length thereof and comprises the amino acid glutamic acid (E) at position 99 using the numbering according to SEQ ID NO. 2. Most particularly preferably, the protease b1) includes an amino acid sequence that corresponds to SEQ ID NO. 2 at positions 1-98 and 100-269 using the numbering according to SEQ ID NO. 2 and comprises the amino acid glutamic acid (E) at position 99. Such a protease is indicated in SEQ ID NO. 4.

Further preferred cleaning agents according to the invention are characterized in that the protease b2) comprises an amino acid sequence that is at least 98% identical to the amino acid sequence indicated in SEQ ID NO. 2 over the entire length thereof and includes the amino acid substitutions R99E, S3T, V4I and V199I using the numbering according to SEQ ID NO. 2. Most particularly preferably, the protease b2) includes an amino acid sequence according to SEQ ID NO. 2 having the amino acid substitutions R99E, S3T, V4I and V199I using the numbering according to SEQ ID NO. 2. Such a protease is indicated in SEQ ID NO. 5.

Preferred cleaning agents according to the invention are furthermore characterized in that the protease b3) comprises an amino acid sequence that is at least 98% identical to the amino acid sequence indicated in SEQ ID NO. 1 over the entire length thereof and includes the amino acid substitution S99A using the numbering according to BPN' in combination with an insertion between positions 99 and 100, wherein the inserted amino acid is Asp (D). Most particularly preferably, the protease b3) includes an amino acid sequence according to SEQ ID NO. 1 having the amino acid substitution S99A in combination with an insertion of the amino acid Asp (D) between positions 99 and 100, in each case using the numbering according to BPN'.

Preferred combinations of proteases are in particular the combination of the protease including the amino acid sequence indicated in SEQ ID NO. 3 with a protease including one of the amino acid sequences indicated in SEQ ID NO. 4, SEQ ID NO. 5 or SEQ ID NO. 6.

In different embodiments, these combinations of proteases are used in a mass ratio of 10:1 to 1:10, preferably 5:1 to 1:5, based on active protein. Particularly preferably, the protease including the amino acid sequence indicated in SEQ ID NO. 3 is used with the protease including the amino acid sequence indicated in SEQ ID NO. 4 in a mass ratio of 10:1 to 1:10, preferably 5:1 to 1:5, in particular 2:1 to 1:2, particularly preferably in equal parts. Further particularly preferably, the protease including the amino acid sequence indicated in SEQ ID NO. 3 is used with the protease including the amino acid sequence indicated in SEQ ID NO. 5 in a mass ratio of 10:1 to 1:10, preferably 5:1 to 1:5, in particular 2:1 to 1:2, particularly preferably in equal parts. According to a further particularly preferred embodiment, the protease including the amino acid sequence indicated in SEQ ID NO. 3 is used with the protease including the amino acid sequence indicated in SEQ ID NO. 6 in a mass ratio of 10:1 to 1:10, preferably 5:1 to 1:5, in particular 2:1 to 1:2, particularly preferably in equal parts.

Surprisingly, the combinations of different proteases described herein have the property to improve the performance of the cleaning agent, preferably of the dishwashing agent, by resulting in improved cleaning performance when it comes to tenacious, burnt soiling. The increase in cleaning performance can also be observed at low temperatures, which is to say temperatures that are lower than those customarily used in dishwashing methods, as defined above. This makes it possible to carry out the cleaning method, preferably the automatic dishwashing method, at lower temperatures and nonetheless preserve the good cleaning performance.

The improvement in cleaning performance shall in general be understood to mean that the removal of soiling, in particular burnt soiling, from hard surfaces, in particular dishes, is noticeably improved when using the cleaning agents described herein for cleaning the same, preferably in an automatic dishwasher, compared to the use of cleaning agents, preferably dishwashing agents, that do not contain the enzyme combinations described herein.

The enzymes to be used can furthermore be formulated together with by-products, such as from fermentation, or with stabilizers.

The cleaning agents, in particular dishwashing agents, preferably contain each protease in a quantity from $1\times10^{-8}$ to 5 wt. %, based on the respective active protein. Preferably 0.001 to 2 wt. %, more preferably 0.005 to 1.5 wt. %, still more preferably 0.01 to 1 wt. %, and particularly preferably 0.01 to 0.5 wt. % of each enzyme is preferably present in these agents.

In particularly preferred embodiments, the first protease is used in the agents described herein in a total quantity from 0.01 to 1 wt. %, preferably 0.025 to 0.5 wt. %, based on active protein. Similarly, the second protease is preferably used in a total quantity from 0.005 to 0.75 wt. %, preferably 0.01 to 0.5 wt. %, based on active protein. Preferably 0.025 to 0.5 wt. % of the protease having the sequence of SEQ ID NO. 3 is used as the first protease, and preferably 0.01 to 0.5 wt. % of the protease having the sequence of SEQ ID NO. 4 is used as the second protease. In a further preferred embodiment, preferably 0.025 to 0.5 wt. % of the protease having the sequence of SEQ ID NO. 3 is used as the first protease, and preferably 0.01 to 0.5 wt. % of the protease having the sequence of SEQ ID NO. 5 is used as the second protease. According to a further, likewise preferred embodiment, preferably 0.025 to 0.5 wt. % of the protease having the sequence of SEQ ID NO. 3 is used as the first protease, and preferably 0.01 to 0.5 wt. % of the protease having the sequence of SEQ ID NO. 6 is used as the second protease.

In liquid formulations, the enzymes are preferably used in the form of liquid enzyme formulation(s).

The protein concentration can be determined using known methods, such as the BCA method (bicinchoninic acid; 2,2-bichinolyl-4,4'-dicarbonic acid) or the biuret method. The active protein concentration is determined in this regard by a titration of the active centers using a suitable irreversible inhibitor (for proteases, for example, phenylmethylsulfonyl fluoride (PMSF)) and determination of the residual activity (see M. Bender et al., J. Am. Chem. Soc. 88, 24 (1966), pgs. 5890-5913).

In particular during storage, the proteases can be protected against damage, such as inactivation, denaturing or disintegration, for example due to physical influences, oxidation or proteolytic cleavage. Inhibiting proteolysis is particularly preferred in the case of microbial production. The described agents may contain stabilizers for this purpose.

Proteases with cleaning action are generally not provided in form of the pure protein, but rather in the form of stabilized, storable and transportable preparations. These preformulated preparations include, for example, solid preparations obtained by way of granulation, extrusion or lyophilization or, in particular in the case of liquid or gel-like agents, solutions of the enzymes, advantageously concentrated to the extent possible, low-hydrate and/or mixed with stabilizers or other auxiliary agents.

Alternatively, the enzymes can be encapsulated, both for the solid and the liquid packaging format, for example by spray drying or extruding the enzyme solution together with a preferably natural polymer, or in the form of capsules, for example those in which the enzymes are enclosed as in a solidified gel, or in those of the core-shell type, in which an enzyme-containing core is coated with a protective layer impervious to water, air and/or chemicals. Additional active agents, such as stabilizers, emulsifiers, pigments, bleaching agents or dyes can additionally be applied in superimposed layers. Such capsules are applied using methods that are known per se, for example agitation or roll granulation or in fluid bed processes. Such granules are advantageously low-dust, for example by applying polymeric film formers, and storage-stable due to the coating.

It is furthermore possible to formulate two or more enzymes together, so that individual granules have multiple enzyme activities.

As is apparent from the comments above, the enzyme protein forms only a fraction of the total weight of customary enzyme preparations. Preferably used protease preparations contain between 0.1 and 40 wt. %, preferably between 0.2 and 30 wt. %, particularly preferably between 0.4 and 20 wt. %, and in particular between 0.8 and 15 wt. % of the enzyme protein. The described agents thus preferably comprise such enzyme preparations in each case in quantities from 0.1 to 10 wt. %, preferably 0.2 to 5 wt. %, based on the total agent.

The cleaning agents described herein, in particular the preferred automatic dishwashing agents, can be of a solid or liquid nature, and in particular be present as powdery solids, in post-compacted particle form, as homogeneous solutions or suspensions. In a further preferred embodiment of the invention, the automatic dishwashing agent is present in preportioned form. In a further preferred embodiment of the invention, the automatic dishwashing agent comprises multiple compositions that are physically separated from each other, whereby it is possible to separate incompatible ingredients from each other, or to offer compositions in combinations, which are used at different points in time in the dishwasher. This is particularly advantageous when the automatic dishwashing agents are present in preportioned form. At least one of the compositions may be present in solid form and/or at least one of the compositions may be present in liquid form, wherein the proteases are present in at least one of the compositions, but may also be present in multiple compositions.

The agents described herein preferably comprise at least one further component, in particular at least two further components, selected from the group consisting of builders, surfactants, polymers, bleaching agents, bleach catalysts, bleach activators, non-protease enzymes, corrosion inhibitors and glass corrosion inhibitors, disintegrants, odorants and perfume carriers.

Possible ingredients are described hereafter, which can advantageously be used in the cleaning agents described herein, in particular dishwashing agents, preferably automatic dishwashing agents.

Advantageously, builders may be used. The builders include in particular zeolites, silicates, carbonates, organic cobuilders and—where ecological bias against their use is absent—also phosphates.

Crystalline layered silicates may be used in the agents described herein. Such cleaning agents, preferably dishwashing agents, in particular automatic dishwashing agents, preferably contain a weight fraction of crystalline layered silicate from 0.1 to 20 wt. %, preferably from 0.2 to 15 wt. %, and in particular from 0.4 to 10 wt. %, in each case based on the total weight of these agents.

It is also possible to use the generally known phosphates as builder substances, provided that such use should not be avoided for ecological reasons. Among the plurality of commercially available phosphates, alkali metal phosphates have the greatest significance in the laundry or cleaning agent industry, pentasodium and pentapotassium triphosphate (sodium or potassium tripolyphosphate) being particularly preferred.

Alkali metal phosphates is the term that covers all the alkali metal (in particular sodium and potassium) salts of the different phosphoric acids, in which a distinction can be made between metaphosphoric acids $(HPO_3)_n$ and orthophosphoric acid $H_3PO_4$, in addition to higher molecular weight representatives. The phosphates combine several advantages: They act as alkali carriers, prevent limescale deposits on machine parts or lime scaling on woven fabrics, and additionally contribute to the cleaning performance.

Technically particularly important phosphates are pentasodium triphosphate, $Na_5P_3O_{10}$ (sodium tripolyphosphate), and the corresponding potassium salt pentapotassium triphosphate, $K_5P_3O_{10}$ (potassium tripolyphosphate). The sodium potassium tripolyphosphates are preferably used.

If within the scope of the present application phosphates are used as substances with washing or cleaning action in the cleaning agents, preferably dishwashing agents, in particular in the automatic dishwashing agent, preferred agents comprise this (these) phosphate(s), preferably alkali metal phosphate(s), particularly preferably pentasodium or pentapotassium triphosphate (sodium or potassium tripolyphosphate), in quantities from 5 to 80 wt. %, preferably from 15 to 75 wt. %, and in particular from 20 to 70 wt. %, in each case based on the weight of the cleaning agent, preferably dishwashing agent, in particular automatic dishwashing agent.

Other builders are the alkali carriers. For example, alkali metal hydroxides, alkali metal carbonates, alkali metal hydrogen carbonates, alkali metal sesquicarbonates, the described alkali silicates, alkali metal silicates and mixtures of the above-mentioned substances are considered alkali carriers, wherein within the meaning of the present invention preferably the alkali carbonates, in particular sodium carbonate, sodium hydrogen carbonate or sodium sesquicarbonate, can be used. A builder system containing a mixture of tripolyphosphate and sodium carbonate is particularly preferred. A builder system containing a mixture of tripolyphosphate and sodium carbonate and sodium silicate is likewise particularly preferred. Due to the low chemical compatibility of the optional alkali metal hydroxides with the remaining ingredients of cleaning agents, in particular dishwashing agents, preferably automatic dishwashing agents, compared to other builder substances, they are preferably used only in small quantities or not at all.

The use of carbonate(s) and/or hydrogen carbonate(s), preferably alkali carbonate(s), particularly preferably sodium carbonate, in quantities from 2 to 50 wt. %, preferably from 5 to 40 wt. %, and in particular from 7.5 to 30 wt. %, in each case based on the weight of the agent, preferably automatic dishwashing agent, is particularly preferred. Agents that, based on the weight of the automatic dishwashing agent, contain less than 20 wt. %, especially less than 17 wt. %, preferably less than 13 wt. %, and in particular less than 9 wt. % carbonate(s) and/or hydrogen carbonate(s), preferably alkali carbonate(s), particularly preferably sodium carbonate, are particularly preferred.

In particular, polycarboxylates/polycarboxylic acids, polymeric polycarboxylates, aspartic acid, polyacetals, dextrins, further organic cobuilders and phosphonates shall be mentioned as organic cobuilders. These substance classes are described hereafter.

Usable organic builder substances are, for example, the polycarboxylic acids that can be used in the form of the free acid and/or of the sodium salts thereof, wherein polycarboxylic acids shall be understood to mean those carboxylic acids that carry more than one acid function. These include, for example, citric acid, adipic acid, succinic acid, glutaric acid, malic acid, tartaric acid, maleic acid, fumaric acid, saccharic acids, nitrilotriacetic acid (NTA), provided that such use is not objectionable for ecological reasons, and mixtures thereof. In addition to the builder effect, the free acids typically also have the property of being an acidifying component and are thus also used as agents to set a lower and milder pH value. In particular, citric acid, succinic acid, glutaric acid, adipic acid, gluconic acid and arbitrary mixtures of these shall be mentioned here.

The use of citric acid and/or citrates in these agents has proven to be particularly advantageous for the cleaning and rinsing performance of agents described herein. Preferred are therefore cleaning agents, preferably dishwashing agents, particularly preferably automatic dishwashing agents, characterized in that the agent contains citric acid or a salt of citric acid, and the weight fraction of the citric acid or of the salt of citric acid especially is more than 10 wt. %, preferably more than 15 wt. %, and in particular between 20 and 40 wt. %.

Aminocarboxylic acids and/or the salts thereof are another significant class of phosphate-free builders. Particularly preferred representatives of this class are methylglycine diacetic acid (MGDA) or the salts thereof, and glutamine diacetic acid (GLDA) or the salts thereof or ethylenediamine diacetic acid (EDDS) or the salts thereof. The content of these amino carboxylic acids or of the salts thereof can amount to between 0.1 and 15 wt. %, preferably between 0.5 and 10 wt. %, and in particular between 0.5 and 6 wt. %, for example. Aminocarboxylic acids and the salts thereof can be used together with the above-mentioned builders, in particular also with the phosphate-free builders.

Builders moreover include polymeric polycarboxylates; for example, these are the alkali metal salts of polyacrylic acid or of polymethacrylic acid, for example those having a relative molar mass from 500 to 70000 g/mol. Suitable polymers are in particular polyacrylates, which preferably have a molar mass from 2000 to 20000 g/mol. Due to the superior solubility thereof, short-chain polyacrylates having molar masses from 2000 to 10000 g/mol, and particularly preferably from 3000 to 5000 g/mol, may in turn be preferred from this group.

Also suitable are copolymeric polycarboxylates, in particular those of acrylic acid with methacrylic acid, and of acrylic acid or methacrylic acid with maleic acid.

The (co)polymeric polycarboxylates can be used either as a powder or as an aqueous solution. The content of (co) polymeric polycarboxylates in the cleaning agents, preferably dishwashing agents, in particular automatic dishwashing agents, is preferably 0.5 to 20 wt. %, and in particular 3 to 10 wt. %.

To improve water solubility, the polymers can also contain allyl sulfonic acids, such as allyloxybenzene sulfonic acid and methallyl sulfonic acid, as a monomer. Further preferred copolymers are those that contain acrolein and acrylic acid/acrylic acid salts or acrolein and vinylacetate as monomers.

Moreover, all compounds that are able to form complexes with alkaline earth ions can be used as builders.

The agents described herein may comprise surfactants, wherein the non-ionic, anionic, cationic and amphoteric surfactants are included in the group of surfactants.

All non-ionic surfactants known to the person skilled in the art may be used as non-ionic surfactants. Suitable non-ionic surfactants are, for example, alkyl glycosides of the general formula $RO(G)_x$, where R corresponds to a primary straight-chain or methyl-branched, in particular methyl-branched at the 2-position, aliphatic group having 8 to 22, preferably 12 to 18 carbon atoms, and G is the symbol that denotes a glycose unit having 5 or 6 carbon atoms, preferably glucose. The degree of oligomerization x, which indicates the distribution of monoglycosides and oligoglycosides, is an arbitrary number between 1 and 10; x is preferably 1.2 to 1.4.

Another class of non-ionic surfactants that can preferably be used, which can be used either as the sole non-ionic surfactant or in combination with other non-ionic surfactants, is alkoxylated, preferably ethoxylated or ethoxylated and propoxylated fatty acid alkyl esters, preferably having 1 to 4 carbon atoms in the alkyl chain.

Non-ionic surfactants of the amine oxide type, for example N-cocoalkyl-N—N-dimethylamine oxide and N-tallowalkyl-N,N-dihydroxyethylamine oxide, and of the fatty acid alkanolamide type may also be suitable. The quantity of these non-ionic surfactants is preferably no more than that of the ethoxylated fatty alcohols, in particular no more than half thereof.

Further suitable surfactants are polyhydroxyfatty acid amides, also known as PHFA.

Low-foaming non-ionic surfactants can be used as preferred surfactants. With particular preference, the cleaning agents, preferably dishwashing agents, in particular automatic dishwashing agents contain non-ionic surfactants from the group of alkoxylated alcohols. Alkoxylated, advantageously ethoxylated, in particular primary alcohols having preferably 8 to 18 carbon atoms and on average 1 to 12 mol ethylene oxide (EO) per mol of alcohol, in which the alcohol residue can be linear or preferably methyl-branched at the 2-position, or can contain linear and methyl-branched residues in the mixture, such as those usually present in oxo alcohol groups, are preferably used as nonionic surfactants. However, alcohol ethoxylates having linear groups of alcohols of native origin having 12 to 18 carbon atoms, for example of coconut, palm, tallow fatty or oleyl alcohol, and an average of 2 to 8 mol EO per mol of alcohol are particularly preferred. The preferred ethoxylated alcohols include, for example, $C_{12-14}$ alcohols having 3 EO or 4 EO, $C_{9-11}$ alcohol having 7 EO, $C_{13-15}$ alcohols having 3 EO, 5 EO, 7 EO, or 8 EO, $C_{12-18}$ alcohols having 3 EO, 5 EO, or 7 EO, and mixtures thereof, such as mixtures of $C_{12-14}$ alcohol having 3 EO and $C_{12-18}$ alcohol having 5 EO. The degrees of ethoxylation indicated represent statistical averages that can correspond to an integer or a fractional number for a specific product. Preferred alcohol ethoxylates exhibit a restricted distribution of homologs (narrow range ethoxylates, NRE). In addition to these non-ionic surfactants, fatty alcohols having more than 12 EO can also be used. Examples of these are tallow fatty alcohol having 14 EO, 25 EU, 30 EO, or 40 EQ.

Non-ionic surfactants that have a melting point above room temperature are particularly preferred. Non-ionic surfactant(s) having a melting point above 20° C., preferably above 25° C., particularly preferably between 25 and 60° C., and in particular between 26.6 and 43.3° C., is/are particularly preferred.

Surfactants that are preferably to be used come from the groups of alkoxylated non-ionic surfactants, in particular ethoxylated primary alcohols.

Anionic surfactants can likewise be used as a component of cleaning agents, preferably dishwashing agents, in particular automatic dishwashing agents. These include in particular alkylbenzene sulfonates, (fatty) alkyl sulfates, (fatty) alkyl ether sulfates, and alkanesulfonates. The anionic surfactant content of the agents is usually 0 to 10 wt. %.

Cationic and/or amphoteric surfactants can also be used instead of or in conjunction with the mentioned surfactants. In cleaning agents, in particular dishwashing agents, preferably automatic dishwashing agents, the content of cationic and/or amphoteric surfactants is especially less than 6 wt. %, preferably less than 4 wt. %, most particularly preferably less than 2 wt. %, and in particular less than 1 wt. %. Agents that contain no cationic or amphoteric surfactants are particularly preferred.

The group of polymers includes in particular polymers with washing or cleaning action, for example rinse polymers and/or polymers acting as softeners. In addition to non-ionic polymers, in general cationic, anionic, and amphoteric polymers can also be used in automatic dishwashing agents.

“Cationic polymers” within the meaning of the present invention are polymers that carry a positive charge in the polymer molecule. This charge can be implemented, for example, by way of (alkyl)ammonium groupings or other positively charged groups that are present in the polymer chain. Particularly preferred cationic polymers come from the groups of quaternized cellulose derivatives, polysiloxanes having quaternary groups, cationic guar derivatives, polymeric dimethyldiallylammonium salts and the copolymers thereof with esters and amides of acrylic acid and methacrylic acid, copolymers of vinylpyrrolidone with quaternized derivatives of dialkylaminoacrylate and -methacrylate, vinylpyrrolidone/methoimidazolinium chloride copolymers, quaternized polyvinyl alcohols, or the polymers described by the INCI names polyquaternium 2, polyquaternium 17, polyquaternium 18, and polyquaternium 27.

“Amphoteric polymers” within the meaning of the present invention further comprise negatively charged groups or monomer units, in addition to a positively charged group, in the polymer chain. These groups can be, for example, carboxylic acids, sulfonic acids or phosphonic acids.

Amphoteric polymers that are preferably used come from the group of alkylacrylamide/acrylic acid copolymers, alkylacrylamide/methacrylic acid copolymers, alkylacrylamide/methylmethacrylic acid copolymers, alkylacrylamide/acrylic acid/alkyl aminoalkyl(meth)acrylic acid copolymers, alkylacrylamide/methacrylic acid/alkylaminoalkyl(meth) acrylic acid copolymers, alkylacrylamide/methylmethacrylic acid/alkylaminoalkyl(meth)acrylic acid copolymers, alkylacrylamide/alkyl methacrylate/alkylamino ethyl methacrylate/alkyl methacrylate copolymers, and copolymers of unsaturated carboxylic acids, cationically derivatized unsaturated carboxylic acids, and optionally further ionic or non-ionogenic monomers.

Preferred zwitterionic polymers come from the group of acrylamidoalkyltrialkylammonium chloride/acrylic acid copolymers and the alkali and ammonium salts thereof, acrylamidoalkyltrialkylammonium chloride/methacrylic acid copolymers and the alkali and ammonium salts thereof, and methacroylethylbetaine/methacrylate copolymers.

Cleaning agents, in particular dishwashing agents, preferably automatic dishwashing agents, preferably contain the above-mentioned cationic and/or amphoteric polymers in quantities between 0.1 and 10 wt. %, in each case based on the total weight of the automatic dishwashing agent. However, automatic dishwashing agents in which the weight fraction of cationic and/or amphoteric polymers is between 0.01 and 8 wt. %, especially between 0.01 and 6 wt. %, preferably between 0.01 and 4 wt. %, particularly preferably between 0.01 and 2 wt. %, and in particular between 0.01 and 1 wt. %, based in each case on the total weight of the automatic dishwashing agent, are preferred within the scope of the present application.

Bleaching agents can furthermore be used in the cleaning agents, preferably dishwashing agents, in particular automatic dishwashing agents. Among the compounds that serve as bleaching agents and yield $H_2O_2$ in water, sodium percarbonate, sodium perborate tetrahydrate, and sodium perborate monohydrate are of particular importance. Further usable bleaching agents are, for example, peroxypyrophosphates, citrate perhydrates, and peracid salts or peracids that yield $H_2O_2$, such as perbenzoates, peroxophthalates, diperazelaic acid, phthaloimino peracid, or diperdodecanedioic acid. All further inorganic or organic peroxy bleaching agents known from the prior art to the person skilled in the art may also be used.

Substances that release chlorine or bromine can also be used as bleaching agents. Among the suitable materials releasing chlorine or bromine, for example, heterocyclic N-bromamides and N-chloramides, such as trichloroisocyanuric acid, tribromoisocyanuric acid, dibromoisocyanuric acid, and/or dichloroisocyanuric acid (DICA), and/or the salts thereof with cations such as potassium and sodium can be considered. Hydantoin compounds, such as 1,3-dichloro-5,5-dimethylhydantoin, are likewise suitable.

Cleaning agents, preferably dishwashing agents, in particular automatic dishwashing agents that contain 1 to 35 wt. %, preferably 2.5 to 30 wt. %, particularly preferably 3.5 to 20 wt. %, and in particular 5 to 15 wt. % bleaching agent, preferably sodium percarbonate, are preferred.

The cleaning agents, preferably dishwashing agents, in particular automatic dishwashing agents can furthermore contain bleach catalysts. The usable bleach catalysts include, but are not limited to, the group of the bleach-boosting transition metal salts and transition metal complexes, preferably the Mn, Fe, Co, Ru or Mo complexes, particularly preferably from the group of the manganese and/or cobalt salts and/or complexes, in particular the cobalt (ammine) complexes, the cobalt (acetate) complexes, the cobalt (carbonyl) complexes, the chlorides of cobalt or manganese, manganese sulfate and the complexes of manganese with 1,4,7-trimethyl-1,4,7-triazacyclononane (Mn3-TACN) or 1,2,4,7-tetramethyl-1,4,7-triazacyclononane (Mn4-TACN).

Cleaning agents, preferably dishwashing agents, in particular automatic dishwashing agents that contain 0.001 to 1 wt. %, preferably 0.01 to 0.1 wt. % bleach catalyst, preferably an Mn complex, in particular a complex of manganese with 1,4,7-trimethyl-1,4,7-triazacyclononane (Mn3-TACN) or 1,2,4,7-tetramethyl-1,4,7-triazacyclononane (Mn4-TACN) are preferred.

In various embodiments of the invention, the cleaning agents, preferably dishwashing agents, in particular automatic dishwashing agents, additionally contain at least one bleach activator. Compounds that, under perhydrolysis conditions, yield aliphatic peroxocarboxylic acids having preferably 1 to 10 carbon atoms, in particular 2 to 4 carbon atoms, and/or optionally substituted perbenzoic acid, can be used as bleach activators. Out of all bleach activators known to a person skilled in the art from the prior art, polyacylated alkylenediamines, in particular tetra acetyl ethylene diamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoyl succinimide (NOSI), acylated phenolsulfonates, in particular n-nonanoyl or iso-nonanoyl oxybenzene sulfonate (n- or iso-NOBS), are particularly preferred. It is also possible to use combinations of conventional bleach activators. These bleach activators are preferably used in quantities of up to 10 wt. %, in particular 0.1 wt. % to 8 wt. %, particularly 2 to 8 wt. %, and particularly preferably 2 to 6 wt. %, based in each case on the total weight of the bleach activator-containing agent.

The agents of the present invention preferably contain at least one additional enzyme preparation or enzyme composition, which contains or more non-protease enzymes. Such enzymes include, without being limited thereto, amylases, lipases, cellulases, hemicellulases, mannanases, pectin-cleaving enzymes, tannanases, xylanases, xanthanases, ß-glycosidases, carrageenanases, perhydrolases, oxidases, oxidoreductases, and the mixtures thereof. Preferred enzymes comprise in particular amylases, in particular alpha-amylases, cellulases, lipases, hemicellulases, in particular pectinases, mannanases, ß-glucanases, and the mixtures thereof. Amylases and/or lipases and the mixtures thereof are particularly preferred. These enzymes are, in principle, of natural origin; proceeding from the natural molecules, improved variants are available for use in washing or cleaning agents and can be used in a correspondingly preferred fashion.

The information provided on quantities and formulation forms in connection with the proteases used apply mutatis mutandis also to all further above-described enzymes.

Glass corrosion inhibitors prevent the appearance of clouding, streaking, and scratching, but also iridescence of the glass surface of automatically cleaned glassware. Preferred glass corrosion inhibitors come from the group of magnesium and zinc salts and of the magnesium and zinc complexes. Within the scope of the present invention, the content of zinc salt in cleaning agents, preferably dishwashing agents, in particular automatic dishwashing agents, is especially between 0.1 and 5 wt. %, preferably between 0.2 and 4 wt. %, and in particular between 0.4 and 3 wt. %, or the content of zinc in oxidized formed (calculated as $Zn^{2+}$) is between 0.01 and 1 wt. %, especially between 0.02 and 0.5 wt. %, and in particular between 0.04 and 0.2 wt. %, in each case based on the total weight of the glass corrosion inhibitor-containing agent.

So as to facilitate the breakdown of prefabricated shaped bodies, it is possible to incorporate disintegration excipients, known as tablet disintegrants, into these agents in order to shorten breakdown times. Tablet disintegrants or breakdown accelerators are understood to mean excipients that ensure rapid breakdown of tablets in water or other media, and the quick release of the active agents. Disintegration excipients can preferably be used in quantities from 0.5 to 10 wt. %, preferably 3 to 7 wt. %, and in particular 4 to 6 wt. %, in each case based on the total weight of the agent comprising the disintegration excipient.

Individual odorous substance compounds, such as synthetic products of the ester, ether, aldehyde, ketone, alcohol, and hydrocarbon types, can be used within the scope of the present invention as perfume oils or odorants. Preferably, however, mixtures of different odorous substances are used, which together produce an appealing odorous note. Such perfume oils can also contain natural odorous substance mixtures such as those accessible from plant sources, for example pine, citrus, jasmine, patchouli, rose, or ylang ylang oil.

Cleaning agents described herein, preferably dishwashing agents, in particular automatic dishwashing agents can be formulated in a variety of ways. The agents can be present in solid or liquid presentation forms or as a combination of solid and liquid presentation forms. Suitable solid presentation forms are, in particular, powders, granules, extrudates, compactates, in particular tablets. The liquid presentation forms based on water and/or organic solvents can be present in thickened form, in the form of gels. Agents described herein can be formulated in the form of single-phase or multi-phase products.

Cleaning agents described herein, preferably dishwashing agents, in particular automatic dishwashing agents, are preferably preformulated as closing units. These closing units preferably comprise the quantity of substances with washing or cleaning action necessary for one cleaning cycle.

The cleaning agents described herein, preferably dishwashing agents, in particular automatic dishwashing agents, in particular the prefabricated closing units, particularly preferably comprise a water-soluble wrapping.

The water-soluble wrapping is preferably formed of a water-soluble film material selected from the group consisting of polymers or polymer mixtures. The wrapping can be formed of one layer or of two or more layers of the water-soluble film material. The water-soluble film material of the first layer and that of the further layers, if such are present, can be the same or different. Films that can be bonded and/or sealed after they have been filled with the agent to form packagings such as tubes or cushions, are particularly preferred.

It is preferable for the water-soluble wrapping to comprise polyvinyl alcohol or a polyvinyl alcohol copolymer. Water-soluble wrappings comprising polyvinyl alcohol or a polyvinyl alcohol copolymer exhibit good stability and sufficiently high water solubility, in particular cold water solubility.

Suitable water-soluble films for producing the water-soluble wrapping are preferably based on a polyvinyl alcohol, or a polyvinyl alcohol copolymer, having a relative molar mass in the range from 10,000 to 1,000,000 $gmol^{-1}$, preferably from 20,000 to 500,000 $gmol^{-1}$, particularly preferably from 30,000 to 100,000 $gmol^{-1}$, and in particular from 40,000 to 80,000 $gmol^{-1}$.

The polyvinyl alcohol is typically produced by the hydrolysis of polyvinyl acetate since the direct synthesis pathway is not possible. The same applies to polyvinyl alcohol copolymers produced accordingly from polyvinyl acetate copolymers. It is preferred if at least one layer of the water-soluble wrapping comprises a polyvinyl alcohol having a degree of hydrolysis of 70 to 100 mole %, preferably 80 to 90 mole %, particularly preferably 81 to 89 mole %, and in particular 82 to 88 mole %.

Additionally, a polymer selected from the group consisting of (meth)acrylic acid-containing (co)polymers, polyacrylamides, oxazoline polymers, polystyrene sulfonates, polyurethanes, polyesters, polyethers, polylactic acid or mixtures of the above polymers can be added to a polyvinyl alcohol-containing film material that is suitable for producing the water-soluble wrapping. A preferred additional polymer is polylactic acids.

In addition to vinyl alcohol, preferred polyvinyl alcohol copolymers comprise dicarboxylic acids as further monomers. Suitable dicarboxylic acids are itaconic acid, malonic acid, succinic acid and mixtures thereof, itaconic acid being preferred.

Likewise preferred polyvinyl alcohol copolymers include an ethylenically unsaturated carboxylic acid, the salt thereof, or the ester thereof, in addition to vinyl alcohol. In addition to vinyl alcohol, such polyvinyl alcohol copolymers particularly preferably comprise acrylic acid, methacrylic acid, acrylic acid esters, methacrylic acid esters or mixtures thereof.

It may be preferred for the film material to contain further additives. For example, the film material may contain plasticizers such as dipropylene glycol, ethylene glycol, diethylene glycol, propylene gylcol, glycerol, sorbitol, mannitol or mixtures thereof. Examples of further additives include release aids, fillers, cross-linking agents, surfactants, antioxidants, UV absorbers, anti-blocking agents, non-stick agents or mixtures thereof.

Suitable water-soluble films for use in the water-soluble wrappings of the water-soluble packagings according to the invention are films sold by MonoSol LLC, for example, by the designation M8630, C8400 or M8900. Other suitable films include films by the designation Solublon® PT, Solublon® GA, Solublon® KC or Solublon® KL from Aicello Chemical Europe GmbH, or the VF-HP films from Kuraray.

A further object of the invention is also the corresponding use of the agents described herein. The invention also relates to a dishwashing method, in particular an automatic dishwashing method, in which an agent according to the invention is used. A further object of the present application is therefore moreover a method for cleaning dishes in an automatic dishwasher, in which the agent is dispensed into the interior of an automatic dishwasher while a dishwashing program is being executed, before the main washing cycle begins, or during the course of the main washing cycle. The dispensing or introduction of the agent into the interior of the automatic dishwasher can take place manually, but preferably the agent is dispensed into the interior of the automatic dishwasher by means of the closing chamber. In the various embodiments of the invention, the (washing) temperature in such dishwashing methods is preferably 50° C. or lower, particularly preferably 45° C. or lower, still more preferably 40° C. or lower.

A typical basic formula for a preferably usable automatic dishwashing agent, for example in tablet form, comprises the following substances:

| | |
|---|---|
| sodium tripolyphosphate | 20 to 50 wt. % |
| sodium carbonate | 10 to 30 wt. % |
| sodium percarbonate | 5 to 18 wt. % |
| bleach activator | 0.5 to 5 wt. % |
| bleach catalyst | 0.01 to 1 wt. % |
| sulfopolymer | 2.5 to 15 wt. % |
| polycarboxylate | 0.1 to 10 wt. % |
| non-ionic surfactant | 0.5 to 10 wt. % |
| phosphonate | 0.5 to 5 wt. % |
| proteases | 0.1 to 5 wt. % |
| amylase | 0.1 to 5 wt. % |

wherein the information in wt. % in each case is based on the total agent. Instead of tripolyphosphate, or a portion of the tripolyphosphate, it is in particular possible to also use 10 to 50 wt. % citrate or MGDA or GLDA or EDDS or mixtures of two or three of these substances in the formula.

EXAMPLES

Example 1: Improving the Protease Performance During Automatic Dishwashing

In a Bosch SMS86 automatic dishwasher, china plates containing soiling of black tea, egg yolk, ground meat and crème brûlée were washed at 40° C. ("Gentle 40" program) and 21° dH using a solid dishwashing tablet (20 g; for composition, see Table 1) comprising various individual proteases (comparison experiments V1 to V5) or protease combinations (M1 to M3). The cème brûlée soiling served as tenacious soiling. For this purpose, the ready-made crème brûlée mixture from Debic was heated in a pot to 60° C., and 3.5 g was applied in each case to a dessert plate using a brush and allowed to dry at room temperature for 2 hours. The plates were then placed into a cold oven (Binder) and heated to 140° C. within 1 hour. The crème brûlée soiling was then burnt-in for 2 hours in the oven at 140° C.

The cleaning performance was visually determined according to IKW (Getman Cosmetic, Toiletry, Perfumery and Detergent Association) after each washing cycle (evaluation from 1 to 10; the higher the value, the better the performance; differences of at least 1 are significant). The results for the tested formulas are listed in Table 2 as arithmetic means. Higher values indicate better cleaning performance.

TABLE 1

| Composition of the automatic dishwashing agent | |
|---|---|
| | Base |
| Phosphate (wt. %) | 35.9 |
| Sodium carbonate (wt. %) | 12.2 |
| Phosphonate (wt. %) | 2.4 |
| Sulfonic acid group-containing polymer | 7.9 |
| Polyacrylate (wt. %) | 4.6 |
| Non-ionic surfactants (wt. %) | 6.1 |
| Percarbonate (wt. %) | 14.6 |
| TAED (wt. %) | 2.3 |
| Bleach catalyst (wt. %) | 1.0 |
| Polycarboxylate (wt. %) | 1.5 |
| Sodium silicate/polycarboxylate (wt. %) | 3.9 |
| Enzyme composition (amylase) (wt. %) | 1.0 |
| Zinc acetate (wt. %) | 0.2 |
| Remainder (perfume, dyes, proteaseor protease mixture etc.) (wt. %) | up to 100 |

The quantity of the corresponding protease preparation (individual proteases, V1 to V5) or of the mixtures thereof (M1 to M3) added to the formulation according to Table 1 was such that the total protease quantity in the formation was 0.24 wt. %.

V1: base+enzyme according to SEQ ID NO. 3

V2: base+enzyme according to SEQ ID NO. 4

V3: base+enzyme according to SEQ ID NO. 5

V4: base+enzyme according to SEQ ID NO. 6

V5: base+Savinase Ultra Plus 16L (Novozymes)

M1: base+mixture in equal parts, based on the protease content in wt. %, made of enzyme according to SEQ ID NO. 3 and enzyme according to SEQ ID NO. 4

M2: base+mixture in equal parts, based on the protease content in wt. %, made of enzyme according to SEQ ID NO. 3 and enzyme according to SEQ ID NO. 5

M3: base+mixture in equal parts, based on the protease content in wt. %, made of enzyme according to SEQ ID NO. 3 and enzyme according to SEQ ID NO. 6

TABLE 2

| Cleaning performance | | | | |
|---|---|---|---|---|
| Protease/protease combination | Tea | Ground meat | Egg yolk | Crème brulee |
| V1 | 8.7 | 10.0 | 5.8 | 4.6 |
| V2 | 5.6 | 9.8 | 6.9 | 8.4 |
| V3 | 6.3 | 10.0 | 5.7 | 7.8 |
| V4 | 6.8 | 9.8 | 5.1 | 8.8 |
| V5 | 5.1 | 10.0 | 6.0 | 5.2 |
| M2 | 8.6 | 9.8 | 6.3 | 8.7 |
| V1 | 9.5 | 9.7 | 6.3 | 4.1 |
| M1 | 8.7 | 9.5 | 6.1 | 6.8 |
| M3 | 9.3 | 9.7 | 6.2 | 7.6 |

As is apparent in Table 2, the protease according to SEQ ID NO. 3 (V1) exhibits very good cleaning performance when it comes to tea soiling, while cleaning performance is only mediocre when it comes to crème brûlée. In contrast, it is apparent that the proteases according to SEQ ID NOS. 4, 5 and 6 (V2 to V4) have good performance when it comes to crème brûlée, while performance is only mediocre when it comes to tea. Savinase (V5) does not exhibit good performance for either tea or crème brûlée.

As can be seen for all tested protease combinations according to the invention, both tea cleaning performance and crème brûlée cleaning performance are at a high level. It is clearly apparent in Table 2 that the combination of two different proteases results in a considerable improvement of the cleaning performance (M1 to M3).

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cleaning agent, comprising at least one first protease and one second protease, wherein:

the said first protease comprises the amino acid sequence of SEQ ID NO: 3, and said second protease comprises the amino acid sequence of SEQ ID NO: 5, wherein said first and said second protease have protease activity.

2. The cleaning agent of claim 1, wherein the weight fraction of each of said proteases, based on the corresponding active protein, in the total weight of said agent is from $1\times10^{-8}$ to 5 wt. %.

3. The cleaning agent of claim 1, comprising at least one further component selected from the group consisting of builders, surfactants, polymers, bleaching agents, bleach catalysts, bleach activators, non-protease enzymes, corrosion inhibitors, glass corrosion inhibitors, disintegrants, oderants and perfume carriers.

4. A method for cleaning dishes in an automatic dishwasher, wherein a cleaning agent claim 1 is dispensed into the interior of an automatic dishwasher while a dishwashing program is being executed, before a main washing cycle begins, or during the course of a main washing cycle.

* * * * *

SEQUENCE LISTING

```
<160> NUMBER OF SEQ ID NOS: 6

<210> SEQ ID NO 1
<211> LENGTH: 269
<212> TYPE: PRT
<213> ORGANISM: Bacillus lentus

<400> SEQUENCE: 1

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

-continued

<210> SEQ ID NO 2
<211> LENGTH: 269
<212> TYPE: PRT
<213> ORGANISM: Bacillus lentus

<400> SEQUENCE: 2

Ala Gln Ser Val Pro Trp Gly Ile Ser Arg Val Gln Ala Pro Ala Ala
1 5 10 15

His Asn Arg Gly Leu Thr Gly Ser Gly Val Lys Val Ala Val Leu Asp
20 25 30

Thr Gly Ile Ser Thr His Pro Asp Leu Asn Ile Arg Gly Gly Ala Ser
35 40 45

Phe Val Pro Gly Glu Pro Ser Thr Gln Asp Gly Asn Gly His Gly Thr
50 55 60

His Val Ala Gly Thr Ile Ala Ala Leu Asn Asn Ser Ile Gly Val Leu
65 70 75 80

Gly Val Ala Pro Ser Ala Glu Leu Tyr Ala Val Lys Val Leu Gly Ala
85 90 95

Asp Gly Arg Gly Ala Ile Ser Ser Ile Ala Gln Gly Leu Glu Trp Ala
100 105 110

Gly Asn Asn Gly Met His Val Ala Asn Leu Ser Leu Gly Ser Pro Ser
115 120 125

Pro Ser Ala Thr Leu Glu Gln Ala Val Asn Ser Ala Thr Ser Arg Gly
130 135 140

Val Leu Val Val Ala Ala Ser Gly Asn Ser Gly Ala Ser Ser Ile Ser
145 150 155 160

Tyr Pro Ala Arg Tyr Ala Asn Ala Met Ala Val Gly Ala Thr Asp Gln
165 170 175

Asn Asn Asn Arg Ala Ser Phe Ser Gln Tyr Gly Ala Gly Leu Asp Ile
180 185 190

Val Ala Pro Gly Val Asn Val Gln Ser Thr Tyr Pro Gly Ser Thr Tyr
195 200 205

Ala Ser Leu Asn Gly Thr Ser Met Ala Thr Pro His Val Ala Gly Ala
210 215 220

Ala Ala Leu Val Lys Gln Lys Asn Pro Ser Trp Ser Asn Val Gln Ile
225 230 235 240

Arg Asn His Leu Lys Asn Thr Ala Thr Ser Leu Gly Ser Thr Asn Leu
245 250 255

Tyr Gly Ser Gly Leu Val Asn Ala Glu Ala Ala Thr Arg
260 265

<210> SEQ ID NO 3
<211> LENGTH: 269
<212> TYPE: PRT
<213> ORGANISM: Artificial
<220> FEATURE:
<223> OTHER INFORMATION: Optimized B. lentus subtilisin 309 variant

<400> SEQUENCE: 3

Ala Gln Ser Val Pro Trp Gly Ile Arg Arg Val Gln Ala Pro Thr Ala
1 5 10 15

His Asn Arg Gly Leu Thr Gly Ser Gly Val Lys Val Ala Val Leu Asp
20 25 30

Thr Gly Ile Ser Thr His Pro Asp Leu Asn Ile Arg Gly Gly Ala Ser
35 40 45

Phe Val Pro Gly Glu Pro Ser Thr Gln Asp Gly Asn Gly His Gly Thr
50 55 60

-continued

```
His Ala Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asp Gly Thr Ser Met Ala Thr Pro His Val Ala Gly Ala
    210                 215                 220

Ala Ala Leu Val Lys Gln Lys Asn Pro Ser Trp Ser Asn Val Arg Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 4
<211> LENGTH: 269
<212> TYPE: PRT
<213> ORGANISM: Artificial
<220> FEATURE:
<223> OTHER INFORMATION: Optimized B. lentus alkaline protease variant

<400> SEQUENCE: 4

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Glu Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160
```

-continued

```
Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 5
<211> LENGTH: 269
<212> TYPE: PRT
<213> ORGANISM: Artificial
<220> FEATURE:
<223> OTHER INFORMATION: Optimized B. lentus alkaline protease variant

<400> SEQUENCE: 5

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Glu Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255
```

-continued

```
Tyr Gly Ser Gly Leu Val Asn Ala Glu Ala Ala Thr Arg
            260                 265


<210> SEQ ID NO 6
<211> LENGTH: 270
<212> TYPE: PRT
<213> ORGANISM: Artificial
<220> FEATURE:
<223> OTHER INFORMATION: Optimized B. lentus subtilisin 309 variant

<400> SEQUENCE: 6

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ala Asp Gly Ser Val Ser Ser Ile Ala Gln Gly Leu Glu Trp
            100                 105                 110

Ala Gly Asn Asn Gly Met His Val Ala Asn Leu Ser Leu Gly Ser Pro
        115                 120                 125

Ser Pro Ser Ala Thr Leu Glu Gln Ala Val Asn Ser Ala Thr Ser Arg
    130                 135                 140

Gly Val Leu Val Val Ala Ala Ser Gly Asn Ser Gly Ala Gly Ser Ile
145                 150                 155                 160

Ser Tyr Pro Ala Arg Tyr Ala Asn Ala Met Ala Val Gly Ala Thr Asp
                165                 170                 175

Gln Asn Asn Asn Arg Ala Ser Phe Ser Gln Tyr Gly Ala Gly Leu Asp
            180                 185                 190

Ile Val Ala Pro Gly Val Asn Val Gln Ser Thr Tyr Pro Gly Ser Thr
        195                 200                 205

Tyr Ala Ser Leu Asn Gly Thr Ser Met Ala Thr Pro His Val Ala Gly
    210                 215                 220

Ala Ala Ala Leu Val Lys Gln Lys Asn Pro Ser Trp Ser Asn Val Gln
225                 230                 235                 240

Ile Arg Asn His Leu Lys Asn Thr Ala Thr Ser Leu Gly Ser Thr Asn
                245                 250                 255

Leu Tyr Gly Ser Gly Leu Val Asn Ala Glu Ala Ala Thr Arg
            260                 265                 270
```